United States Patent [19]
Ankerhold et al.

[11] Patent Number: 5,767,976
[45] Date of Patent: Jun. 16, 1998

[54] LASER DIODE GAS SENSOR

[75] Inventors: Georg Ankerhold; Ralf Buchtal, both of Lübeck, Germany

[73] Assignee: Drägerwerk AG, Lübeck, Germany

[21] Appl. No.: 780,205

[22] Filed: Jan. 8, 1997

[30] Foreign Application Priority Data

Mar. 22, 1996 [DE] Germany ............... 196 11 290.7

[51] Int. Cl.$^6$ .................... G01N 21/31; G01N 21/35
[52] U.S. Cl. .............. 356/437; 250/338.5; 356/438
[58] Field of Search .................... 356/437, 438; 250/338.5

[56] References Cited

U.S. PATENT DOCUMENTS

| | | | |
|---|---|---|---|
| 4,126,396 | 11/1978 | Hartmann et al. | 356/438 X |
| 5,002,391 | 3/1991 | Wolfrum et al. | 356/437 X |
| 5,202,570 | 4/1993 | Tanaka et al. | 250/575 |
| 5,339,155 | 8/1994 | Partridge et al. | 356/419 |
| 5,545,517 | 8/1996 | Thompson et al. | 356/73.1 X |

FOREIGN PATENT DOCUMENTS

| | | | |
|---|---|---|---|
| 25 21 934 B2 | 3/1978 | Germany. | |
| 41 10 095 A1 | 10/1992 | Germany. | |
| 57-22538 | 2/1982 | Japan | 356/437 |
| 58-213237 | 12/1983 | Japan | 356/437 |
| 2 245 058 | 12/1991 | United Kingdom. | |

OTHER PUBLICATIONS

H. Riris, C. B. Carlisle, L. W. Carr, De. E. Cooper, R. U. Martinelli, and R. J. Menna, Oct. 20, 1994, Design of an open path near-infrared diode laser sensor: application to oxygen, water, and carbon dioxide vapor detection, 1994 Optical Society of America, Applied Optics, vol. 33, No. 30.

Henrik Ahlberg, Stefan Lundqvist, Robert Tell and Torbjörn Andersson, 1994, Laser spectroscopy for in situ ammonia monitoring, LASER SPECTROSCOPY Spectroscopy Europe 1994.

H. I. Schiff, S. D. Nadler and G. I. Mackay, 1995, The Lasair–New Remote Sensing Instruments Based on Near Infrared Diode Lasers, SPIE vol. 2366, pp. 65–69.

*Primary Examiner*—Vincent P. McGraw
*Attorney, Agent, or Firm*—McGlew and Tuttle

[57] ABSTRACT

A laser diode gas sensor for the spectroscopic measurement of a gas sample, with a retroreflector and a concave mirror, which define between them an open measuring path with the gas to be analyzed. Laser light passes through the measuring path, is reflected at the retroreflector, and is directed toward a detector via a concave mirror in order to determine the mean concentration of the gas component to be analyzed in the optical measuring path. Optical elements, such as beam splitters, lenses, etc., which lead to losses of intensity, were used before to couple the laser light into the beam path onto the retroreflector, and to decouple the reflected light to the detector. An improved optical imaging array, which minimizes losses, is provided. The concave mirror is provided centrally with an opening transparent to the laser light, through which a weakly divergent bundle of laser light is directed onto the retroreflector, so that the retroreflector is illuminated essentially over its entire surface. The retroreflector is made with a matrix consisting of a plurality of triple mirrors, which reflect the incident, weakly divergent bundle of laser beams as a bundle of laser beams with convergent properties onto the concave mirror. The concave mirror is arranged or shaped such that the laser light reflected by the retroreflector is focused by the concave mirror directly onto the detector, which is arranged outside the principal beam path.

20 Claims, 5 Drawing Sheets

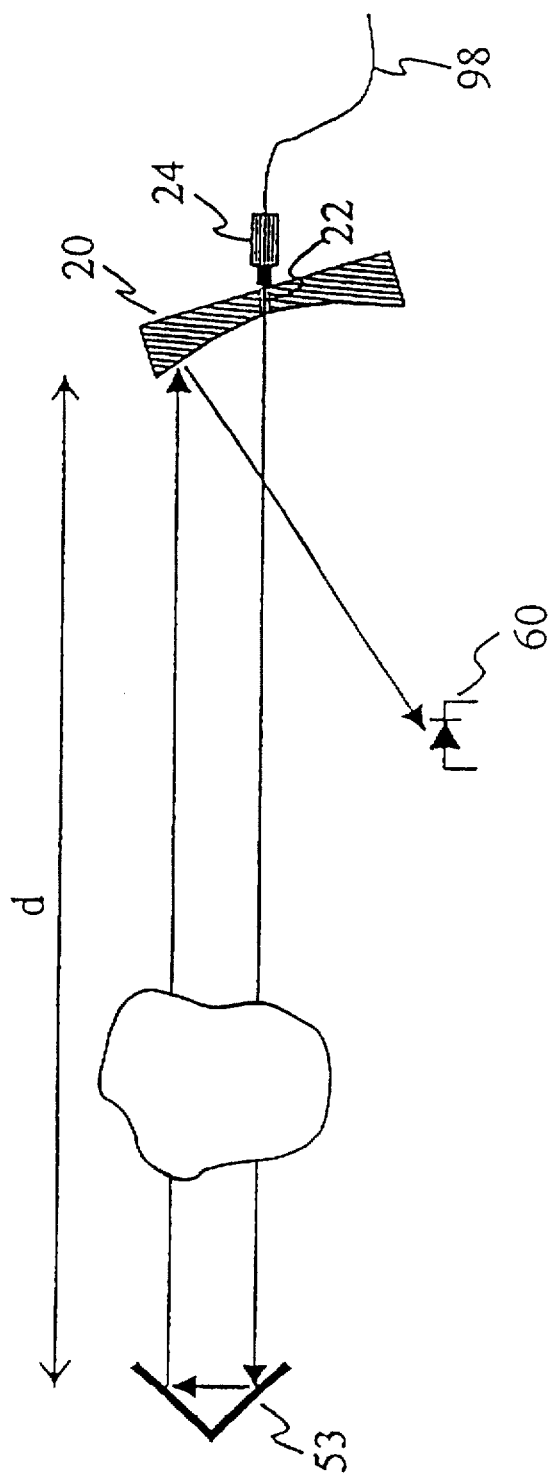

LASER DIODE GAS SENSOR

FIELD OF THE INVENTION

The present invention pertains to a laser diode gas sensor with an open optical measuring path and more particularly to a laser diode gas sensor for the spectroscopic measurement of at least one component of a gas sample, with a retroreflector and with a concave mirror, which define between them a measuring path with the gas sample to be analyzed, with a laser diode, which directs laser light onto the retroreflector, and with a reflector, to which the laser light reflected by the retroreflector and the concave mirror is directed, in order to determine its intensity after passing through the optical measuring path, and to determine an indicator for the concentration of the gas component to be analyzed on the basis of this intensity.

BACKGROUND OF THE INVENTION

Such a laser diode gas sensor has been known from, e.g., U.S. Pat. No. 5,339,155, in which a gas sensor with open measuring path ("open-path sensor") is described, in which laser light is directed via a beam splitter and an obliquely standing mirror onto a concave mirror and from there as a parallel bundle of beams onto a reflector located at a remote location. The laser light is reflected by the reflector, and the light again travels through the measuring path, after which the reflected laser light again falls onto the concave mirror, which focuses the reflected light on the obliquely standing mirror. The reflected laser light travels from the obliquely standing mirror toward the originally coupled laser light. Part of the reflected laser light is then cast by the beam splitter onto a detector, while another part is lost. This array, consisting of a concave mirror, an obliquely standing output mirror in the focus of the concave mirror, and a detector, corresponds to that of a Newton telescope, with a semitransparent mirror being additionally provided in the beam path to couple laser light and to decouple reflected light onto the detector. Gas sensors with a design corresponding to a Cassegrain telescope have been known as well.

The analysis of gas mixtures has acquired increasing significance in both environmental analysis and process control engineering and monitoring technology. The requirements imposed on the measuring systems in terms of sensitivity, selectivity, long-term stability, maintenance intervals, and service life have been steadily increasing. For example, to recognize a gas occurring in environmental analysis or in monitoring technology as quickly as possible, it is desirable to cover the areas to be monitored over a large area.

A large number of sensors measuring in a locally narrowly limited manner may be used for this purpose, but optically imaging gas sensors, in which the emitted light travels over long measuring paths (long open-path systems) and with which so-called "optical fences" can be formed, are far more effective. Such systems make it possible to obtain data on the average gas concentration in the measuring path. However, only the presence of the gas being sought in the measuring path is usually of interest, but its absolute concentration, which is subjected to local changes, is not, so that the determination of the average gas concentration is sufficient. In addition, the types of gas to be monitored are known in the vicinity of chemical plants, so that the measurement can be limited to certain spectral ranges, in which an absorption line characteristic of the type of gas to be monitored occurs.

Monomode laser diodes are well suited for use as light sources for such measuring systems; the price level of such laser diodes has steadily decreased in the past years due to their increasing use and mass production for applications in the area of communications engineering. They are characterized by a number of advantages over the thermal light sources used previously: (1) They have high spectral intensity, (2) they have excellent beam quality compared with thermal light sources; (3) they have an extraordinarily narrow-band spectral emission range of a few 10 MHz, (4) they offer excellent amplitude and frequency modulation properties, (5) they have a service life of several decades, and (6) a high optical/electrical efficiency.

Based on the good modulation ability, measuring systems with diode lasers can utilize special spectroscopic techniques, such as derivative spectroscopy, and thus they can reach high selectivity and sensitivity of detection for a given type of gas. They can thus be greatly superior to previous measuring systems with differential filters or with a Fourier interferometer. However, derivative spectroscopy is suitable only for gases with a pronounced, sharply structured absorption spectrum.

Laser diodes suitable for the gas-measuring technique—so-called monomode laser diodes with DFB or DBR resonator structure—are manufactured in large numbers for applications in communications engineering, but only in the wavelength ranges around 1,310 nm and 1,550 nm. If such laser diodes are to be used, the measurement is limited to certain gases, e.g., methane, ammonia, hydrogen sulfide, hydrochloric acid, or hydrofluoric acid, which have absorption lines in the above-mentioned spectral ranges.

Since these near-infrared laser diodes have a broad field of application in communications engineering, the corresponding optomechanical elements, such as monomode glass fibers, fiber couplers used as beam splitters, pin-and-socket connectors, etc., are readily available and relatively inexpensive. In addition, inexpensive optical glass elements or protective screens made of glass, which still have a sufficiently good optical transparency in the spectral range, may be used. The individual optical elements can be fitted together in a relatively simple manner without time-consuming adjustment, aside from the setting of the imaging optical system over the measuring path.

After a market has developed in the past years for laser diodes in the telecommunications industry, and the manufacturing processes for monomode DFB laser diodes have been able to be increasingly refined in terms of stability and reproducibility, the development of the first open-path systems with near-infrared laser diodes as gas sensors began a few years ago. "Long open-path" gas sensors are described in, e.g., "Design of an open path near-infrared diode laser sensor: Application to oxygen, water, carbon dioxide vapor detection," H. Riris et al., *Appl. Opt.*, Volume 33, No. 30, p. 7059 (1994), and "Laser spectroscopy for in situ ammonia monitoring," H. Ahlberg et al., *Spectroscopy Europe*, 6/2 (1994). The fundamental physical methods for determining gas concentrations (derivative spectroscopy, FM spectroscopy) have been known for many years and described in numerous publications.

As was mentioned above, a Newton telescope design and a Cassegrain telescope design of gas sensor systems with open measuring path with imaging mirror array have been known. The drawback of the prior-art systems is that optical elements attenuating the radiation, such as mirrors/beam splitters, are located in the principal beam path. This is also true of imaging systems with lenses, e.g., that described in U.S. Pat. No. 5,202,570, so that attenuation of the amount of light sent to the detector for the measurement and consequently of the available output signal occurs. Furthermore, a relatively expensive adjustment is necessary in the prior-art imaging mirror arrays, because a plurality of imaging elements must be aligned in the beam path.

The use of a single triple mirror as a retroreflector with an otherwise usual optical array with mirrors and beam splitters as a beam splitter has been known from H. L Schiff et al., The LASAIR—New Remote Sensing Instruments Based on Near Infrared Diode Lasers, in *SPIE*, Vol. 2366, pp. 65–69. The above-described problems of signal reduction due to optical elements and the expensive adjustment also arise with this prior-art device. Moreover, the use of a single triple mirror as a retroreflector has various drawbacks. A single triple mirror comprises three plane mirrors, which are located at right angles to one another and they enclose the corners of a cube between them. On the one hand, the triple mirror must have a large aperture to be reached by the laser light with certainty, as is indicated in FIG. 5. However, such large triple mirrors are very expensive and difficult to adjust. Furthermore, the retroreflector consisting of a single triple mirror might be irradiated with a collimated bundle of laser beams only, which is parallel or convergent, because the reflected bundle of beams is also divergent in the case of a divergent bundle of beams, so that part of the returning bundle of beams is not caught by the concave mirror. In addition, mechanical inaccuracies in the rectangular alignment of the three individual mirrors of the triple mirror may have drastic effects on the direction of the reflected beams. Moreover, due to the size of the triple mirror, the parallel offset of the reflected beams, which always occurs in triple mirrors and depends on the point of impact of the light beam in question on the triple mirror, is no longer negligible and it leads to losses of reflected light, so that the measured signal is reduced.

SUMMARY AND OBJECTS OF THE PRESENT INVENTION

The primary object of the present invention is to provide an improved open-path gas sensor, whose optical imaging array makes possible a higher sensitivity and simpler adjustment of the gas sensor.

According to the invention, a laser diode gas sensor for the spectroscopic measurement of at least one component of a gas sample is provided with a retroreflector and with a concave mirror, which define between them a measuring path with the gas sample to be analyzed. A laser diode is provided which directs laser light onto the retroreflector, and with a reflector, to which the laser light reflected by the retroreflector and the concave mirror is directed, in order to determine its intensity after passing through the optical measuring path, and to determine an indicator for the concentration of the gas component to be analyzed on the basis of this intensity. The retroreflector has a matrix consisting of a plurality of triple mirrors. The concave mirror is provided centrally with an opening which is transparent to the laser light, through which opening the weakly divergent bundle of laser beams is directed onto the retroreflector, so that the triple mirror matrix is illuminated essentially over its entire surface. The concave mirror is arranged or shaped such that the bundle of laser beams reflected by the retroreflector is focused by the concave mirror directly on the detector, which is arranged outside the principal beam path of the bundle of laser beams reflected from the retroreflector.

A retroreflector having a matrix with a plurality of triple mirrors is provided according to the present invention. The triple mirror matrix is illuminated with a bundle of laser beams essentially over its entire surface, and the bundle of laser beams is directed as a weakly divergent bundle of laser beams onto the remote retroreflector through an opening provided centrally in a concave mirror. The triple mirror matrix reflects back the slightly divergent bundle of laser beams as a convergent bundle of laser beams, and it casts it onto the concave mirror. The concave mirror is directed or shaped such that the reflected laser light is focused directly on a detector located outside the principal beam path. No attenuating optical elements, such as beam splitters, or lenses are located in the principal beam path in the array according to the present invention, so that an increased evaluable signal is obtained, and the sensitivity of the sensor is consequently higher or its range is wider. In addition, the adjustment of the gas sensor is simplified, because only one optical element must be adjusted. In contrast to a single triple mirror, the use of a matrix of triple mirrors is insensitive to adjustment. The array according to the present invention also makes possible a more compact design compared with prior-art mirror telescope designs.

The laser light is irradiated as a weakly divergent bundle of beams through an opening which is provided in the concave mirror and is transparent to laser light, the divergence of the bundle of beams being set such that the retroreflector located at a great distance from the concave mirror is illuminated essentially over its entire surface. In order to possibly illuminate the entire surface of the retroreflector, on the one hand, but to make it possible, on the other hand, to irradiate the bundle of laser beams through a relatively small opening in the center of the focusing concave mirror, it is necessary to use a slightly divergent bundle of laser beams, and the divergence angle must be set depending on the distance of the retroreflector. The laser light may be directed onto the retroreflector from, e.g., the laser diode via a glass fiber line and via a collimator, which is arranged at the end of the glass fiber line and is arranged in or directly behind the central opening in the concave mirror. The laser light exiting the glass fiber line in a strongly divergent form is bundled by the collimator to the extent that it is concentrated essentially on the triple mirror matrix.

In a preferred embodiment, the concave mirror is formed by a spherical concave mirror, whose optical axis is tilted against the axis of the bundle of beams traveling from the central opening to the retroreflector such that the bundle of laser light reflected from the retroreflector and falling on the concave mirror is directly focused on a detector located outside the principal beam path. As an alternative, the concave mirror may also be formed by a nonaxial parabolic mirror, i.e., a mirror surface of a parabolic mirror remote from its optical axis, which is shaped such that the bundle of laser beams reflected from the retroreflector is focused on the detector arranged outside the principal beam path between the retroreflector and the concave mirror.

In a preferred embodiment, the triple mirror matrix of the retroreflector is formed by a commercially available plastic retroreflector, as are commonly used as reflectors for photoelectric cells, bicycle reflectors or other rear reflectors, but their rear side, in which a matrix of regularly arranged triple mirror elements had already been embossed at the time of manufacture, rather than their flat front side, is preferably used. To improve the reflection properties, a thin metal layer, e.g., a gold layer, may be applied by vapor deposition. This design of the retroreflector is characterized by especially low cost, because such plastic reflectors are mass-produced.

Even the flat side (front side) of a retroreflector may be selected as the reflection surface in the case of short gas-measuring paths. Even though this leads to an impairment in the reflection properties, a commercially available element can be used without conversion.

The prior-art processes may be used for the signal evaluation with signal evaluation at single (1f), double (2f) and triple (3f) modulation frequency. Furthermore, the so-called "line-locking" by means of a reference cuvette is used to stabilize the wavelength of the laser radiation to the absorption line. It is, moreover, possible to use normalization procedure, as described in U.S. Pat. No. 5,202,570, for the signal evaluation. Since there is a nonlinear relationship between the current modulation and the modulated laser light power emitted, which leads to undesired harmonic waves in the case of a derivative spectroscopic detection method, a power control process, as is described in DE 41 10 095 A1, is preferably used.

Furthermore, a preferred embodiment of the gas sensor has a laser diode emitting in the visible range, whose light can be irradiated into the central opening, i.e., via the first glass fiber line and the collimator in order thus to make possible the alignment of the concave mirror with the retroreflector by the user observing the light spot by means of a telescope and aligning the concave mirror such that the light spot will be possibly exactly directed toward the retroreflector. The phase-sensitive amplified if signal, which is formed by amplitude modulation of the laser light and should always be present even without gas absorption, may be used for a further fine adjustment. The signal may be converted into an acoustic signal, e.g., in a voltage-frequency converter, so that the user can optimize the adjustment on the basis of the pitch of the signal. On the one hand, this type of adjustment offers the advantage that the user does not have to concentrate on an optical display during the adjustment, and, on the other hand, it makes possible a very accurate adjustment, because human hearing is highly sensitive to differences in pitch.

By electing a suitable laser diode, it is possible, in principle, to detect any gas absorbing in the NIR with sharply pronounced line structure. It is therefore also possible to couple laser light from different laser diodes with different wavelengths by means of a so-called "wavelength division multiplexer (glass fiber beam coupler with multiple inputs and one output) into a common glass fiber and thus to measure a plurality of gases with only one sensor array. It would be necessary in this case to provide a plurality of reference gas cuvettes with the corresponding different gases, or one reference cuvette with the corresponding gas mixture. To again separate the signals corresponding to the individual gases from one another, it would be possible to use different modulation frequencies for the individual laser diodes.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a schematic design with a single triple mirror element, which does not represent an embodiment of the present invention, for explaining the function of a single triple mirror.

DESCRIPTION OF THE PREFERRED EMBODIMENTS

Figure 1:
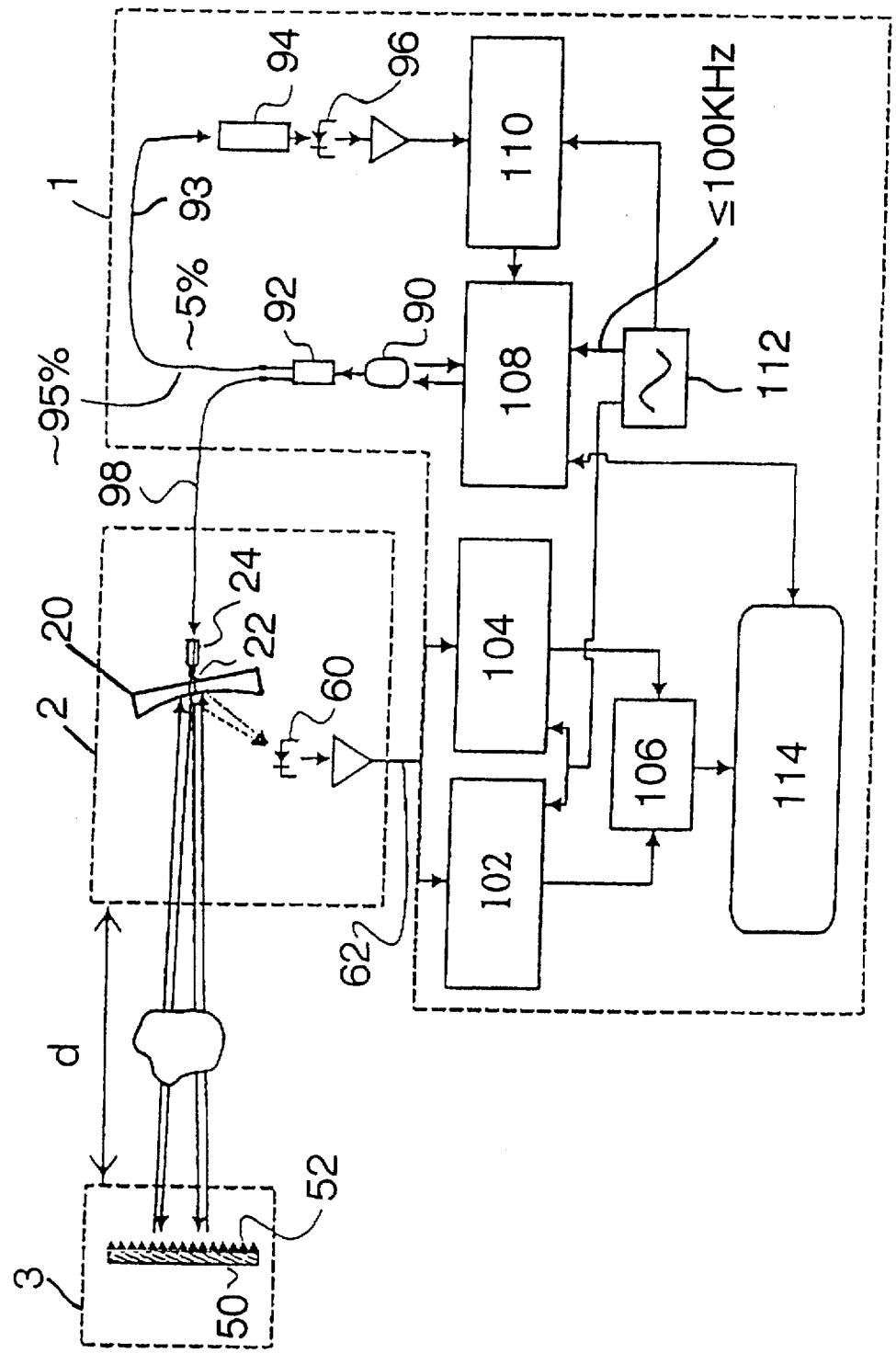
FIG. 1 is a schematic synoptic view of the design of a laser diode gas sensor according to the present invention.

Referring to the drawings in particular, FIG. 1 shows a schematic synoptic view of the laser diode gas sensor according to the present invention. The gas sensor can be divided essentially into three separate principal components: The control and evaluation unit 1, the laser measuring head 2, and the reflector unit 3, wherein an optical measuring path d, which has a length of a few hundred m in the case of typical applications, is located between the laser measuring head 2, and the reflector unit 3. The control and evaluation unit 1, which also contains the laser diode 90, is connected to the laser measuring head 2 via a first glass fiber line 98; there is another connection between the two units in the electric line 62, which sends the signals of the laser measuring head 2 to the control and evaluation unit 1 for evaluation.

In a module, the control and evaluation unit 1 contains a hermetically sealed DFB laser diode 90 with fixed glass fiber connection, which laser diode 90 is associated with a Peltier cooling element, a thermistor, and a monitor diode. A laser diode control device 108 for the power and temperature control of the laser diode 90, a reference gas cuvette 94 containing the gas to be measured, as well as a circuit 104 for the phase-sensitive signal evaluation at single (1f) modulation frequency, a circuit 102 for phase sensitive signal evaluation at double frequency (2f), and a circuit 110 for phase-sensitive signal evaluation at triple modulation frequency (3f) are present as well. The laser diode control device 108 controls the laser diode 90 with sinus modulation of the injection current, which inherently results in amplitude as well as wavelength modulation of the laser light generated by the laser diode 90.

In the case of phase-sensitive rectification, the intensity modulation contributes only to a signal at single modulation frequency (1f). Since this signal is also present in the absence of the gas and it depends only on the laser intensity in the case of weak absorption, it is suitable for signal normalization. Such a normalization is performed in the control and evaluation unit 106. In contrast, the phase-sensitive amplified component due to the wavelength modulation occurs only in the case of gas absorption at the first, second and higher harmonics of the basic frequency, and the 2f signal is an indicator of the mean gas concentration.

The evaluation and control unit 1 also contains a high-frequency generator 112 for the modulation and a processor unit 114, which performs the evaluation and the display of results and general control tasks.

To stabilize the laser radiation of the diode 90 to the spectral transmission minimum of the absorption line (line locking), part of the laser light emitted by the laser diode 90 is decoupled from the principal beam by means of a beam splitter 92 and is sent to a reference gas cuvette 94 via a second glass fiber line 93 and is focused on an InGaAs photodetector 96 by means of a gradient index lens. The splitting into a measuring laser beam and a reference laser beam is performed in the beam splitter 92 by means of a usual fiber coupler, and only a fraction of typically less than 1% of the total optical power of the laser diode 90 is necessary for the reference measurement. The stabilization to the line minimum as a local extreme value is performed by a PI temperature control unit of the chip on which the laser diode is formed, and the zero point of the third derivative, which corresponds to the spectral position of the line minimum, is selected as the desired value of the control.

Since there is a nonlinear relationship between the current modulation and the exiting modulated laser light, which leads to undesired harmonics in the case of the derivative spectroscopic detection method, a power control process, as is described in DE 41 10 095 A1, is preferably used. Signal variations due to external environmental effects, such as rain, fog, contamination of the optically imaging elements or the like, but also due to a change in the light power of the diode, changes in amplitude due to movements of the glass fiber lines, etc., are extensively eliminated due to the normalization of the received signal. The signal normalization $I_2/I_{1f}$ may also be performed by means of a computer, which also assumes the further evaluation, such as the signal filtering, and is thus able to assume the functions of the units 106 and 114, and it finally displays the gas concentration integrated over the travel open d. The normalization procedure is described in, e.g., the above-mentioned U.S. Pat. No. 5,202,570 which is hereby incorporated by reference.

The optical measuring path d is located between the laser measuring head 2 and the retroreflector 3. The laser light of the laser diode 90 is sent to the laser measuring head 2 via the beam splitter 92 and the first glass fiber line 98, which is formed by a monomode glass fiber cable. A commercially available collimator 24 of compact design is arranged at the end of the first glass fiber line 98. The collimator 24 is used to collimate the laser light exiting divergently (divergence angle, e.g., about 15°) from the first glass fiber line 98 to the extent that the slightly divergent bundle of laser beams exiting from the collimator 24 will essentially completely illuminate the surface of the retroreflector 50 after traveling through the measuring path d. The bundle of laser beams exiting from the collimator 24 passes through a central opening 22 in the concave mirror 20, which opening is transparent to the laser light, in order to direct the bundle of beams to the retroreflector 50. The collimator 24 is located immediately behind the concave mirror 20, which is tilted such that the bundle of laser light which exits from the central opening 22 and is reflected back to the concave mirror 20 is directly focused on the detector 60, which is located outside the principal beam path between the retroreflector 50 and the concave mirror.

Figure 2:
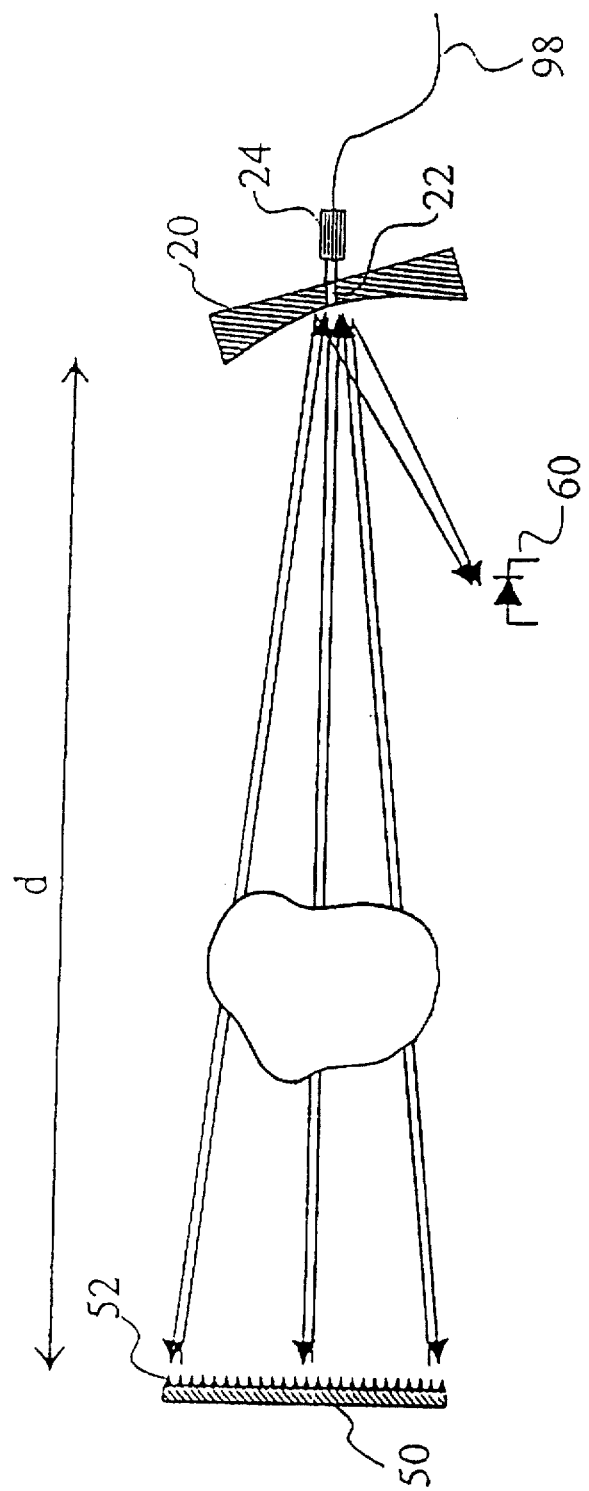
FIG. 2 is a schematic view of the optical elements for explaining the function of the gas sensor according to the present invention.

The retroreflector 50 is formed by a matrix of triple mirrors 52 (FIG. 2). The triple mirrors 52 cover the surface of the retroreflector 50 in a dense and regular array. The triple mirrors 52 have a dimension of a few mm, e.g., in the range of 1 to 5 mm, at their top edges.

As is shown in FIG. 2, the slightly divergent bundle of laser beams from the collimator 24 is reflected at the retroreflector 50 after passing through the optical measuring path d such that it returns to the tilted concave mirror 20 as a convergently reflected bundle of laser beams. This reflection behavior results from the optical properties of a matrix of triple mirrors 52, which reflect an incident light beam in the direction corresponding to the direction of incidence, as can be recognized from, e.g., FIG. 5, aside from an offset, which is on the order of magnitude of the opening of the triple mirror element. Since a retroreflector 50 consisting of a matrix comprising a plurality of triple mirrors 52 is used according to the present invention, the offset during the reflection is practically irrelevant compared with the overall extension of the retroreflector 50, so that the slightly divergent bundle of laser light, which fans out beginning from the collimator 24 to the extent that it illuminates the retroreflector 50 essentially over its entire surface after traveling through the measuring path d, is reflected as a convergent bundle of laser beams to the concave mirror 20, which focuses it on the detector 60 arranged outside the principal beam path because of its tilt angle. As was mentioned above, the triple mirror elements have edge lengths of a few mm, typically 1 to 5 mm, on their opening surface, so that the offset of the beam is practically insignificant compared with the overall surface of the matrix.

Thus, the design described makes possible the illumination of the retroreflector 50 over a large area by means of a divergent bundle of beams, and the bundle has convergent properties after the reflection. The light can therefore be focused on the detector 60 by means of a divergent bundle of beams with little loss. Due to the large-area illumination of the retroreflector 50, local contamination of the reflector, such as rain drops, dust particles or dirt particles, do not lead to any appreciable attenuation of the signal.

An unnecessary attenuation of the evaluable light intensity is avoided, or, in other words, a high output signal level is obtained due to the direct focusing of the reflected bundle of beams by the concave mirror 20 on the detector 60, without an additional, intermediate optical element, so that the optical measuring path d may be very long in the array according to the present invention.

The matrix arrays consisting of triple mirrors 52 can be manufactured at low cost, because flat plastic rear reflectors, which have a regular array of embossed triple mirror elements on their rear side, can be used, and they are available at a relatively favorable cost. The reflection properties may be improved by applying a very thin metal layer, e.g., by vapor depositing a gold layer.

Figure 3:
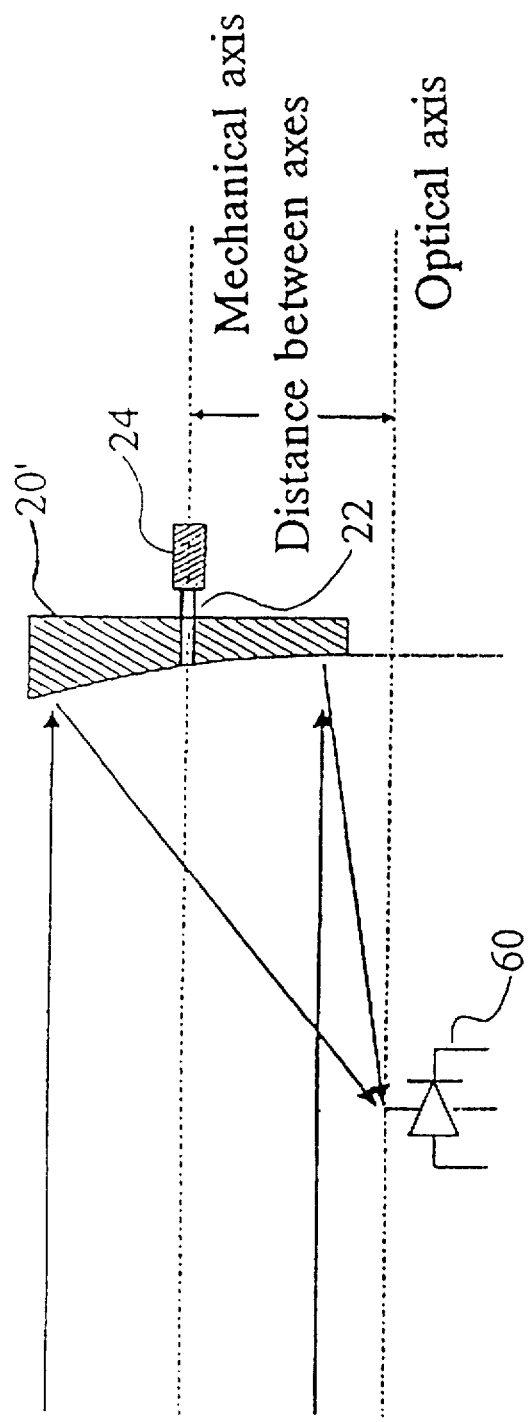
FIG. 3 is a schematic view of an alternative embodiment of a concave mirror for use in the gas sensor.

FIG. 3 shows an alternative embodiment of the concave mirror 20'. The concave mirror 20' is of an asymmetric and nonaxial design, i.e., it is a surface element of a concave mirror remote from the imaginary optical axis of the concave mirror. As a result, incident light is focused on the focus which is located on the imaginary optical axis, outside the principal beam path, and in which the detector 60 is arranged.

Figure 4:
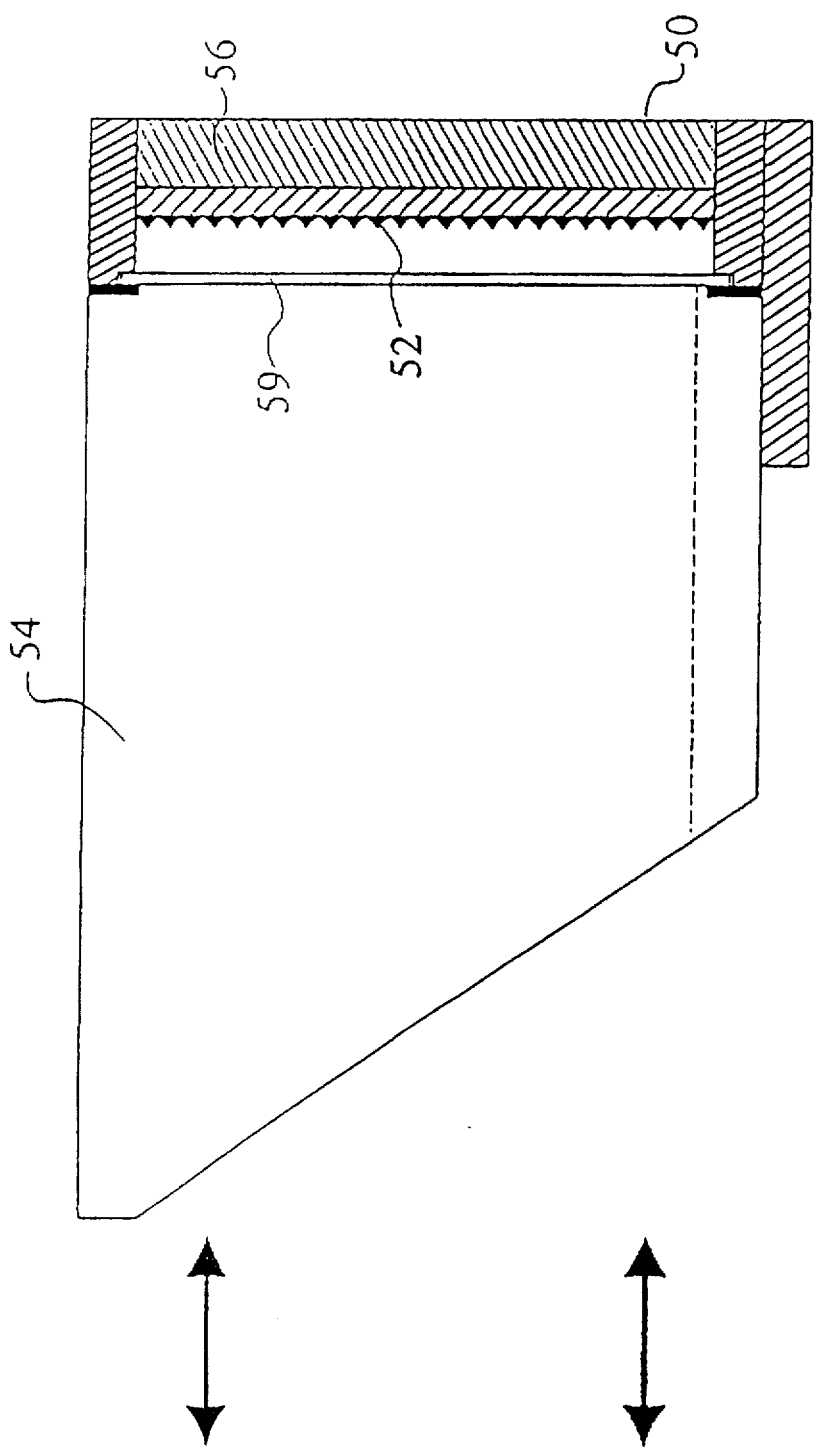
FIG. 4 is a sectional view of an embodiment of the retroreflector.

FIG. 4 shows a retroreflector 50 for the gas sensor. The retroreflector 50 has a regular array or matrix of individual triple mirrors 52 on one side. The triple mirror matrix of the retroreflector 50 is protected by a glass window 59 against external effects. Furthermore, a protective cover 54, which is to protect the glass window 59 from environmental effects and contamination, is provided. The side plate 56 is used as a closure and for mechanical stabilization.

FIG. 5 shows the beam path in the case of illumination with collimated light and a single triple mirror 53. A large aperture is necessary in order for the mirror to be reached by light more or less reliably. Such triple mirrors 53 are expensive and difficult to adjust. This immediately shows the advantages of a matrix array of triple mirrors 52, as is used in the above-described array according to the present invention.

While specific embodiments of the invention have been shown and described in detail to illustrate the application of the principles of the invention, it will be understood that the invention may be embodied otherwise without departing from such principles.

What is claimed is:

1. A laser diode gas sensor for the spectroscopic measurement of at least one component of a gas sample, comprising:
   a retroreflector, said retroreflector including a matrix having a plurality of triple mirrors forming a triple mirror matrix;
   a concave mirror, said retroreflector cooperating with said concave mirror to define between them an optical measuring path with the gas sample to be analyzed;
   a laser diode;
   a detector; and
   laser direction means for directing laser light from said laser diode onto the retroreflector, said laser direction means providing a weekly divergent bundle of laser beams, laser light reflected by the retroreflector being directed by said concave mirror to said detector, in order to determine an intensity of laser light after passing through the optical measuring path, and to determine an indicator for the concentration of the gas component to be analyzed on the basis of said intensity, said concave mirror being provided centrally with an opening transparent to laser light, through which opening said weakly divergent bundle of laser beams is directed onto said retroreflector, so that said triple mirror matrix is illuminated essentially over its entire surface; and said concave mirror is arranged or shaped such that the bundle of laser beams reflected by said retroreflector is focused by said concave mirror directly on said detector, said detector being arranged outside a principal beam path of a bundle of laser beams reflected from said retroreflector.

2. A laser diode gas sensor in accordance with claim 1, wherein an optical axis of said concave mirror is tilted relative to a bundle of beams directed from said central opening onto said retroreflector such that said concave mirror focuses the bundle of laser beams reflected from the said retroreflector directly onto said detector located outside the principal beam path between said retroreflector and said concave mirror.

3. A laser diode gas sensor in accordance with claim 1, wherein said concave mirror is formed by a nonaxial parabolic mirror, which is shaped such that the bundle of laser beams reflected from said retroreflector is focused on said detector, arranged outside a principal beam path between said retroreflector and said parabolic mirror.

4. A laser diode gas sensor in accordance with claim 1, wherein the laser light is directed from said laser diode onto said retroreflector via a first optical fiber line and through a collimator arranged at an end of said optical fiber line through said central opening of said concave mirror.

5. A laser diode gas sensor in accordance with claim 4, further comprising a fiber-optic beam splitter coupling a major part of the laser light of said laser diode into said first optical fiber line and coupling a remaining part of the laser light into a second optical fiber line, said second optical fiber line directing laser light onto a reference cuvette, behind which a photodetector is arranged.

6. A laser diode gas sensor in accordance with claim 1, wherein said triple mirror matrix is at least partially formed of plastic, in the surface of which a regular array of triple mirror elements is embossed, and to which a thin metal layer is applied.

7. A laser diode gas sensor in accordance with claim 6, wherein said metal layer is gold.

8. A laser diode gas sensor in accordance with claim 4, wherein said laser diode operating in the visible wavelength range is present, from which the visible laser light can be coupled into the first glass fiber line in order to optically direct the light beam exiting from said central opening of said concave mirror onto said retroreflector.

9. A laser diode gas sensor in accordance with claim 7, further comprising conversion means for converting a phase-sensitive amplified if signal generated by amplitude modulation of the laser light into an acoustic signal by voltage-frequency conversion, and a control and evaluation unit, said conversion means being provided in said control and evaluation unit, so that a user can optimize the adjustment of the gas sensor on the basis of the pitch of the acoustic signal.

10. A laser diode gas sensor in accordance with claim 1, wherein a plurality of monomode laser diodes operating at a different wavelength and a glass fiber beam coupler with a plurality of inputs and one output are present, wherein one of the laser diodes irradiated on one of the inputs of the glass fiber beam coupler, and the output of the glass fiber beam coupler is connected to said central opening of the said concave mirror in order to direct the superimposed bundle of laser beams of the plurality of laser diodes onto the said retroreflector.

11. A laser diode gas sensor for the spectroscopic measurement of at least one component of a gas sample, comprising:
   a retroreflector, said retroreflector including a matrix having a plurality of triple mirrors forming a triple mirror matrix;
   a concave mirror with a central opening transparent to laser light, said retroreflector cooperating with said concave mirror to define between them an optical measuring path with the gas sample to be analyzed;
   a laser diode;
   a detector;
   laser direction means for directing laser light from said laser diode onto the retroreflector including a first optical fiber line extending from said laser diode and a collimator arranged at an end of said optical fiber line adjacent to said central opening of said concave mirror, said laser direction means providing a weekly divergent bundle of laser beams, laser light reflected by the retroreflector being directed by said concave mirror to said detector, in order to determine an intensity of laser light after passing through the optical measuring path, and to determine an indicator for the concentration of the gas component to be analyzed on the basis of said intensity, said weakly divergent bundle of laser beams being directed through said central opening onto said retroreflector, so that said triple mirror matrix is illuminated essentially over its entire surface and concave mirror being arranged or shaped such that the bundle of laser beams reflected by said retroreflector is focused by said concave mirror directly on said detector, said detector being arranged outside a principal beam path of a bundle of laser beams reflected from said retroreflector.

12. A laser diode gas sensor in accordance with claim 11, wherein an optical axis of said concave mirror is tilted relative to a bundle of beams directed from said central opening onto said retroreflector such that said concave mirror focuses the bundle of laser beams reflected from the said retroreflector directly onto said detector located outside the principal beam path between said retroreflector and said concave mirror.

13. A laser diode gas sensor in accordance with claim 11, wherein said concave mirror is formed by a nonaxial parabolic mirror, which is shaped such that the bundle of laser beams reflected from said retroreflector is focused on said detector, arranged outside a principal beam path between said retroreflector and said parabolic mirror.

14. A laser diode gas sensor in accordance with claim 11, further comprising a fiber-optic beam splitter coupling a major part of the laser light of said laser diode into said first optical fiber line and coupling a remaining part of the laser light into a second optical fiber line, said second optical fiber line directing laser light onto a reference cuvette, behind which a photodetector is arranged.

15. A laser diode gas sensor in accordance with claim 11, wherein said triple mirror matrix is at least partially formed of plastic, in the surface of which a regular array of triple mirror elements is embossed, and to which a thin metal layer is applied.

16. A laser diode gas sensor in accordance with claim 15, wherein said metal layer is gold.

17. A laser diode gas sensor in accordance with claim 11, wherein said laser diode operating in the visible wavelength range is present, from which the visible laser light can be coupled into the first glass fiber line in order to optically direct the light beam exiting from said central opening of said concave mirror onto said retroreflector.

18. A laser diode gas sensor in accordance with claim 16, further comprising conversion means for converting a phase-sensitive amplified 1f signal generated by amplitude modulation of the laser light into an acoustic signal by voltage-frequency conversion, and a control and evaluation unit, said conversion means being provided in said control and evaluation unit, so that a user can optimize the adjustment of the gas sensor on the basis of the pitch of the acoustic signal.

19. A laser diode gas sensor in accordance with claim 11, wherein a plurality of monomode laser diodes operating at a different wavelength and a glass fiber beam coupler with a plurality of inputs and one output are present, wherein one of the laser diodes irradiated on one of the inputs of the glass fiber beam coupler, and the output of the glass fiber beam coupler is connected to said central opening of the said concave mirror in order to direct the superimposed bundle of laser beams of the plurality of laser diodes onto the said retroreflector.

20. A laser diode gas sensor for the spectroscopic measurement of at least one component of a gas sample, comprising:

a retroreflector, said retroreflector including a matrix having a plurality of triple mirrors forming a triple mirror matrix;

a concave mirror, said retroreflector cooperating with said concave mirror to define between them an optical measuring path with the gas sample to be analyzed;

a laser diode;

a detector, said laser diode directing laser light onto the retroreflector, laser light reflected by the retroreflector being directed by said concave mirror to said detector, in order to determine an intensity of laser light after passing through the optical measuring path, and to determine an indicator for the concentration of the gas component to be analyzed on the basis of said intensity, said concave mirror being provided centrally with an opening transparent to laser light, through which opening a weakly divergent bundle of laser beams is directed onto said retroreflector, so that said triple mirror matrix is illuminated essentially over its entire surface; and said concave mirror is arranged or shaped such that the bundle of laser beams reflected by said retroreflector is focused by said concave mirror directly on said detector, said detector being arranged outside a principal beam path of a bundle of laser beams reflected from said retroreflector;

conversion means for converting a phase-sensitive amplified 1f signal generated by amplitude modulation of the laser light into an acoustic signal by voltage-frequency conversion; and a control and evaluation unit, said conversion means being provided in said control and evaluation unit, so that a user can optimize the adjustment of the gas sensor on the basis of the pitch of the acoustic signal.

\* \* \* \* \*